United States Patent
Pui et al.

(10) Patent No.: US 7,655,945 B2
(45) Date of Patent: Feb. 2, 2010

(54) REAL-TIME MONITORING OF PARTICLES IN SEMICONDUCTOR VACUUM ENVIRONMENT

(75) Inventors: David Y. Pui, Plymouth, MN (US); Yi Liu, Minneapolis, MN (US); Christof Asbach, Oberhausen (DE); Heinz Fissan, Kerken-Aledekerk (DE)

(73) Assignee: Regents of the University of Minnesota, St. Paul, MN (US)

( * ) Notice: Subject to any disclaimer, the term of this patent is extended or adjusted under 35 U.S.C. 154(b) by 426 days.

(21) Appl. No.: 11/773,197

(22) Filed: Jul. 3, 2007

(65) Prior Publication Data

US 2009/0206820 A1     Aug. 20, 2009

Related U.S. Application Data

(63) Continuation of application No. 10/814,883, filed on Mar. 31, 2004.

(51) Int. Cl.
   *H01L 23/58*     (2006.01)
(52) U.S. Cl. ............. 257/48; 257/E21.521; 324/71.4; 324/464
(58) Field of Classification Search ........... 324/71.4, 324/464; 257/48, E21.521; 438/1, 17, 18
   See application file for complete search history.

(56) References Cited

U.S. PATENT DOCUMENTS

| | | | |
|---|---|---|---|
| 4,222,045 A | 9/1980 | Cholin | 340/628 |
| 4,400,971 A | 8/1983 | Tassicker | 73/28 |
| 4,598,280 A | 7/1986 | Bradford | 340/631 |
| 5,192,701 A | 3/1993 | Iwasaki | 438/174 |
| 5,247,827 A | 9/1993 | Shah | 73/28.01 |
| 5,440,122 A | 8/1995 | Yasutake | 250/443.1 |
| 5,457,396 A | 10/1995 | Mori et al. | 324/724 |
| 6,043,639 A | 3/2000 | Arrowsmith et al. | 324/71.4 |
| 6,928,892 B2 | 8/2005 | Storbeck et al. | 73/865.8 |
| 7,038,460 B1 | 5/2006 | Skinner | 324/464 |
| 2002/0028399 A1 | 3/2002 | Nakasuji et al. | 430/30 |
| 2004/0031928 A1 | 2/2004 | Smith | 250/380 |
| 2004/0194556 A1 | 10/2004 | Shu et al. | 73/862.045 |
| 2005/0225308 A1 | 10/2005 | Orvek | 324/71.4 |

Primary Examiner—Jarrett J Stark
(74) Attorney, Agent, or Firm—Westman, Champlin & Kelly, P.A.

(57) ABSTRACT

An apparatus includes semiconductor processing equipment. A particle detecting integrated circuit is positioned in a vacuum environment, the particle detecting integrated circuit containing a device having a pair of conductive lines exposed to the vacuum environment. The pair of conductive lines is spaced at a critical pitch corresponding to diameters of particles of interest. A computer system is linked to the particle detecting integrated circuit to detect a change in an electrical property of the conductive lines when a particle becomes lodged between or on the lines.

20 Claims, 2 Drawing Sheets

REAL-TIME MONITORING OF PARTICLES IN SEMICONDUCTOR VACUUM ENVIRONMENT

CROSS-REFERENCE TO RELATED APPLICATIONS

This application is a continuation application of and claims priority to U.S. application Ser. No. 10/814,883, entitled "Real-Time Monitoring of Particles in Semiconductor Vacuum Environment", and filed on Mar. 31, 2004.

TECHNICAL FIELD

This invention relates to real-time monitoring of particles in a semiconductor vacuum environment.

BACKGROUND

A microprocessor is an integrated circuit (IC) built on a tiny piece of silicon. A microprocessor contains millions of transistors interconnected through fine wires made of aluminum or copper.

Microprocessor fabrication is a complex process involving many steps. Microprocessors are typically built by layering materials on top of thin rounds of silicon, called wafers, through various processes using chemicals, gases and light. In chip making, very thin layers of material, in carefully designed patterns, are put on the blank silicon wafers. The patterns are computerized designs that are miniaturized so that up to several hundred microprocessors can be put on a single wafer.

Because the patterns are so small, it is nearly impossible to deposit material exactly where it needs to be on the wafer. Instead, a layer of material is deposited, or grown across an entire wafer surface. Then, the material that is not needed is removed and only the desired pattern remains.

The microprocessor fabrication process begins with "growing" an insulting layer of silicon dioxide on top of a polished wafer in a high temperature furnace.

Photolithography, a process in which circuit patterns are printed on the water surface, is next. A temporary layer of a light sensitive material called a "photoresist" is applied to the wafer. Ultraviolet light shines through clear spaces of a stencil called a "photomask" or "mask" to expose selected areas of the photoresist. Masks are generated during a design phase and are used to define a circuit pattern on each layer of a chip. Exposure to light chemically changes the uncovered portions of the photoresist. The machine used to do this is typically called a "scanner" because it scans one die or a few die at a time, then steps to the next die or set of die until it has exposed the entire wafer.

An active area of the mask is exposed to a vacuum environment of a scanner and is at high risk of accumulating particles. If a particle lands in a critical part of the active area then it will lead to a printed defect on the wafer. This defect causes decreased yields, or increased wafer cost in rework if the defect is fortuitously caught prior to further wafer processing by wafer defect metrology.

DESCRIPTION OF DRAWINGS

Like reference symbols in the various drawings indicate like elements.

DETAILED DESCRIPTION

The systems and techniques described here relate to real-time monitoring of particles in vacuum environments of semiconductor processing equipment. For ease of discussion, a photolithography process of a semiconductor fabrication is used as an example for describing the real-time monitoring of particles in vacuum chambers of semiconductor processing equipment. However, the systems and techniques described herein are not limited to photolithography; rather, they can be used in any semiconductor vacuum process environment in which a real-time monitoring of particles is needed, such as while depositing a film on a semiconductor wafer or implanting a dopant on a semiconductor wafer.

A semiconductor manufacturing process hinges on a use of a photographic process to generate fine featured patterns of an integrated circuit (IC). Each layer of a chip is defined by a specific mask. A mask is somewhat like a photographic negative, which is made by patterning a film of chromium on a pure quartz glass plate. The finished plates are referred to as reticles. Reticles are manufactured by sophisticated and expensive pattern generation equipment, which is driven from a chip design database. The patterns are formed on the chromium plated quartz by removing the chromium with either laser or electron-beam driven tools.

Figure 1:
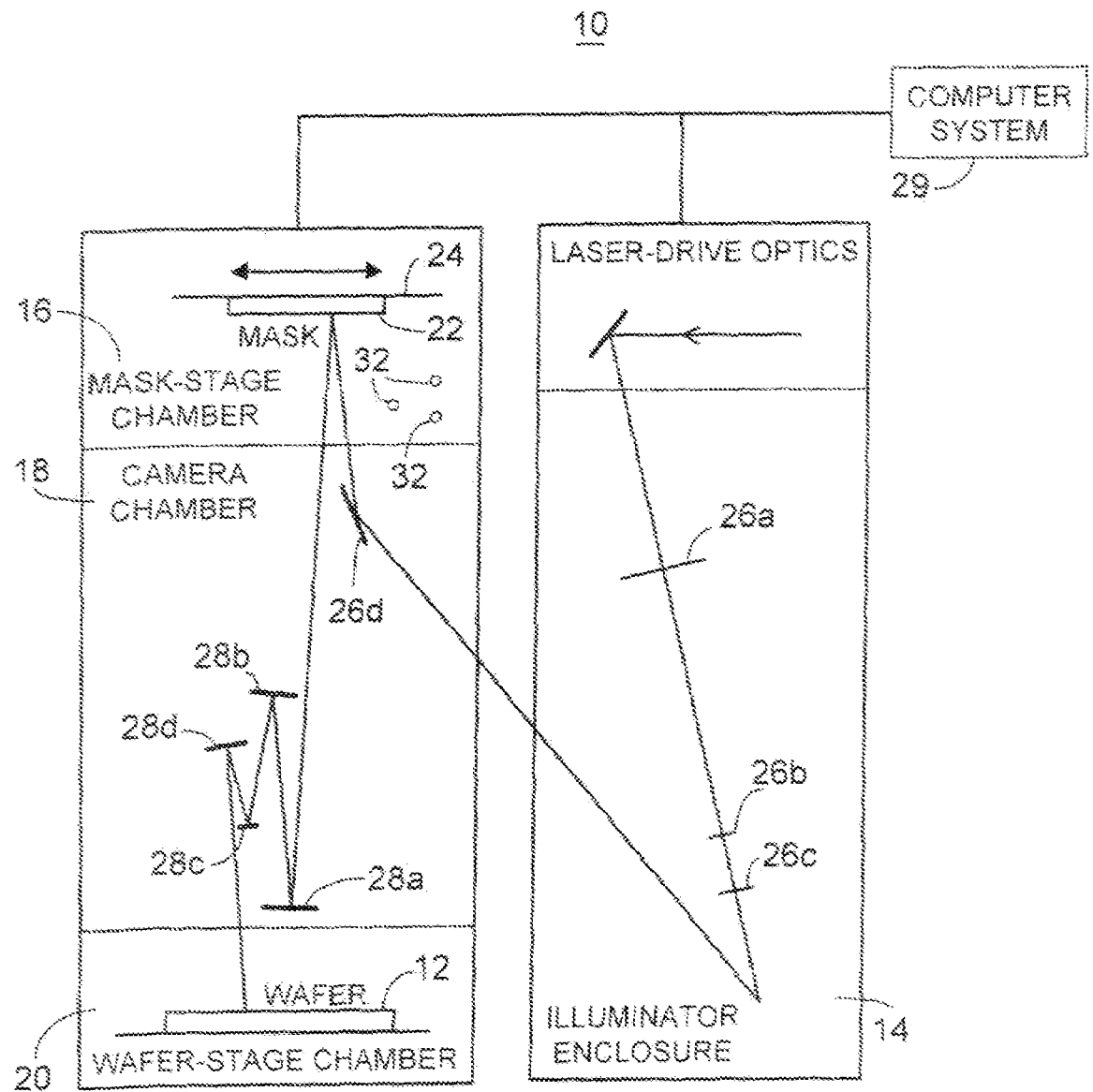
FIG. 1 is a block diagram of an exemplary optical projection lithography system.

Referring to FIG. 1, an exemplary optical projection lithography system 10, such as an extreme-ultraviolet (EUV) lithography system, is shown. Optical projection lithography is the technology used to print the intricate patterns that define integrated circuits into a semiconductor wafer 12. The system 10 includes an illuminator enclosure 14, a mask-stage chamber 16, a camera chamber 18 and a wafer-stage chamber 20.

The illuminator enclosure 14 includes laser optics that, for example, generate EUV light from a plasma generated when a laser illuminates a jet of xenon gas. The light is collected and focused on a mask 22 residing on a mask stage 24 in the mask-stage chamber 16 by a series of condenser mirrors 26a, 26b, 26c, 26d. A mask image is projected onto the wafer 12 by a reduction camera 28a, 28b, 28c, 28d, while the mask 22 and wafer 12 are simultaneously scanned. The entire operation takes place in high-vacuum environmental chambers and is controlled by a computer system 29.

Impurities 32, such as metallic and/or non-metallic particles, can be present in the mask-stage chamber 16. If one of the particles 32 lands on a critical part of an active area of the mask 22 it will lead to a printed defect on the wafer 12. This defect causes decreased yields, or increased wafer cost in rework if the defect is detected at an early stage. The present invention provides a real-time detection of the presence of particles in the vicinity of the mask 22 that would warrant stoppage of the lithography system 10. In an extreme-ultraviolet (EUV) lithography environment, particle sizes that are estimated to be of concern are on the order of 50 nanometers (nm).

Figure 2:
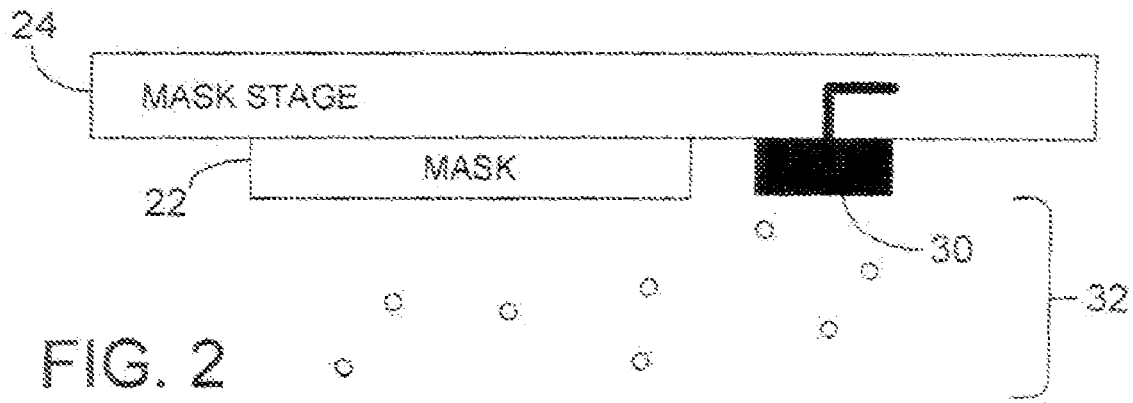
FIG. 2 is a block diagram of a stage.

As shown in FIG. 2, the mask stage 24 includes a placement of one or more active semiconductor components 30 near the mask 22 and embedded within the mask stage 24. The active semiconductor components 30 can include any number of different devices that function to detect particles that land on them.

Figure 3:
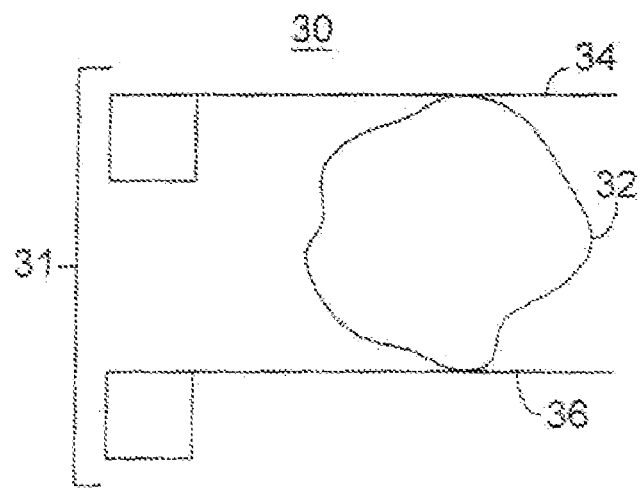
FIG. 3 is a block diagram of an exposed semiconductor component.

As shown in FIG. 3, each active semiconductor component 30 includes one or more devices 31. Each device 31 includes a pair of conductive lines 34, 36 exposed to a local vacuum environment within the mask-stage chamber 16. The conductive lines 34, 36 of the device 31 are spaced at a critical pitch corresponding to the smallest particle diameter of interest. A voltage is applied to the conductive lines 34, 36 of the device 31. A metallic particle having a diameter the size of the pitch between the conductive lines 34, 36, or larger, generates a short in a current flow between the conductive lines 34, 36. A non-metallic particle having a diameter the size of the pitch between the conductive lines 34, 36, or larger, generates a change in capacitance between the conductive lines 34, 36. The short and/or change in capacitance is detected by the computer system 29. Detection of such particle(s) provides a warning that particles are in the vicinity of a critical part of the tool, such as near the mask 22 in this lithography example. When detected, corrective action can be taken, such as terminating the lithography process before the particles cause imperfections in the wafer 12. In one particular embodiment, the short and/or change in capacitance is detected by off-chip circuitry (not shown).

A number of these devices 31 can be located in the semiconductor device 30 providing determination of particle density counts. Devices 31 sensitive to various particle sizes, e.g., by varying the pitch of the pairs of lines, can also be incorporated into the active semiconductor component 30 to monitor a range of particle sizes through a region or regions of interest.

In a particular embodiment, each active semiconductor component 30 is protected by a remote-controlled removable cover (not shown) until the component 30 is ready to be exposed to a vacuum environment. The cover is remotely triggered by the computer system 29 or other triggering mechanism (not shown) to open when desired, exposing the device 31 to the vacuum environment.

Figure 4:
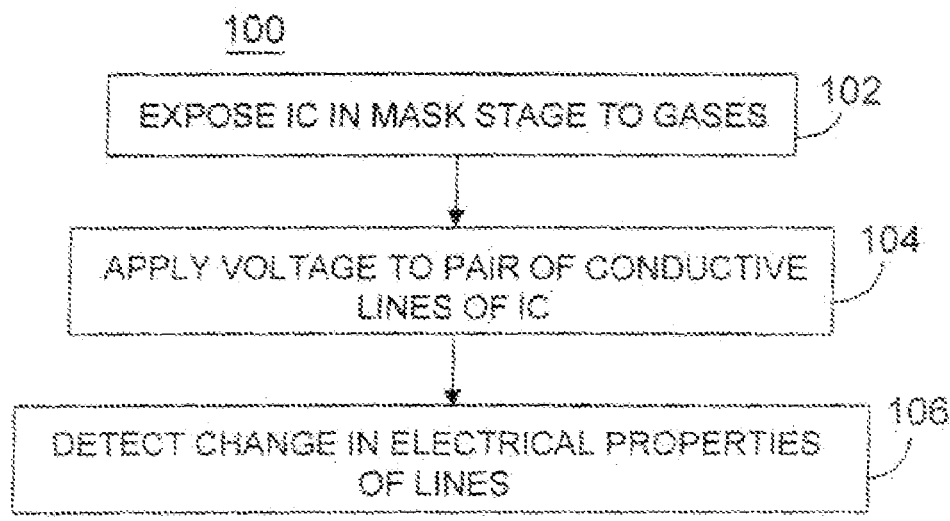
FIG. 4 is a flow diagram of a real-time particle monitoring process.

As shown in FIG. 4, a real-time monitoring process 100 for detecting particles in a semiconductor vacuum environment includes exposing (102) a particle detecting integrated circuit embedded in a stage to residual gases and particles within a vacuum environment. The particle detecting integrated circuit includes a device having a pair of conductive lines spaced at a critical pitch corresponding to diameters of particles of interest.

Process 100 applies (104) a voltage to the pair of conductive lines and detects (106) a change in an electrical property of the conductive lines resulting from a particle landing on or between the pair of conductive lines. A metallic particle having a diameter the size of the pitch between the lines, or larger, generates a short in a current flow between the lines. A non-metallic particle having a diameter the size of the pitch between the lines, or larger, generates a change in capacitance between the lines. The short and/or change in capacitance is detected by the computer system. Once detected, corrective action con be initiated.

Other embodiments are within the scope of the following claims.

What is claimed is:

1. An apparatus comprising:
a vacuum chamber containing a particle detecting integrated circuit, the particle detecting integrated circuit including a plurality of devices, each of the plurality of devices including a pair of conductive lines that are configured to define a channel to capture at least one particle having an associated diameter, the pair of conductive lines of each of the plurality of devices includes a uniform pitch representing a single particle size between pairs of the conductive lines of the plurality of devices;

wherein the pairs of the conductive lines of the plurality of devices are further configured to enable a change in capacitance of one of the pairs of conductive lines of the plurality of devices when a non-metallic particle is lodged on or between the one of the pairs of the conductive lines of the plurality of devices.

2. The apparatus of claim 1 further comprising a computer system linked to the particle detecting integrated circuit.

3. The apparatus of claim 2 wherein the computer system is configured to detect the change in capacitance when the non-metallic particle is lodged on or between the one of the pairs of conductive lines of one of the plurality of devices.

4. The apparatus of claim 1 wherein the particle detecting integrated circuit includes a remote-controlled movable cover protecting the plurality of devices.

5. An apparatus comprising:
a mask stage in a vacuum chamber of semiconductor processing equipment;
a particle detecting integrated circuit embedded in the mask stage, the particle detecting integrated circuit comprising a plurality of devices, each of the plurality of devices having a pair of conductive lines exposed to a local vacuum environment, the pair of conductive lines are configured to define a channel to capture at least one particle having an associated diameter, the pair of conductive lines of each of the plurality of devices having a uniform pitch representing a single particle size;
wherein the pairs of conductive lines of the plurality of devices are further configured to enable a change in capacitance of one of the pairs of conductive lines of the plurality of devices when a non-metallic particle is lodged on or between the one of the pairs of the conductive lines of the plurality of devices.

6. The apparatus of claim 5 wherein the pair of conductive lines of each of the plurality of devices is configured to receive an applied voltage.

7. The apparatus of claim 5 further comprising a computer system linked to the particle detecting integrated circuit.

8. The apparatus of claim 7 wherein the computer system is configured to detect the change in capacitance when the non-metallic particle is lodged on or between the one of the pairs of conductive lines of the plurality of devices.

9. The apparatus of claim 7 wherein the computer system is semiconductor component circuitry.

10. The apparatus of claim 7 wherein the computer system is off-chip circuitry.

11. An apparatus comprising:
a vacuum chamber containing a particle detecting integrated circuit, the particle detecting integrated circuit including a plurality of devices, each of the plurality of devices including a pair of conductive lines that are configured to define a channel to capture at least one particle having an associated diameter, the pair of conductive lines of each of the plurality of devices includes one of a plurality of pitches representing a range of particle sizes between pairs of the conductive lines of the plurality of devices; and
wherein the pairs of conductive lines of the plurality of devices are further configured to enable a change in capacitance of one of the pairs of conductive lines of the plurality of devices when a non-metallic particle is lodged on or between the one of the pairs of the conductive lines of the plurality of devices.

12. The apparatus of claim 11 further comprising a computer system linked to the particle detecting integrated circuit.

13. The apparatus of claim 12 wherein the computer system is configured to detect the change in capacitance when the non-metallic particle is lodged on or between the one of the pairs of the conductive lines of the plurality of devices.

14. The apparatus of claim 11 wherein the particle detecting integrated circuit includes a remote-controlled movable cover protecting the plurality of devices.

15. An apparatus comprising:
- a mask stage in a vacuum chamber of semiconductor processing equipment;
- a particle detecting integrated circuit embedded in the mask stage, the particle detecting integrated circuit comprising a plurality of devices, each of the plurality of devices having a pair of conductive lines exposed to a local vacuum environment, the pair of conductive lines are configured to define a channel to capture at least one particle having an associated diameter, the pair of the conductive lines of each of the plurality of devices having a non-uniform pitch representing a range of particle sizes;
- wherein the pairs of the conductive lines of the plurality of devices are further configured to enable a change in capacitance of one of the pairs of conductive lines of the plurality of devices when a non-metallic particle is lodged on or between the one of the pairs of the conductive lines of the plurality of devices.

16. The apparatus of claim 15 wherein the pair of conductive lines of each of the plurality of devices is configured to receive an applied voltage.

17. The apparatus of claim 15 further comprising a computer system linked to the particle detecting integrated circuit.

18. The apparatus of claim 17 wherein the computer system is configured to detect the change in capacitance when the non-metallic particle is lodged on or between the one of the pairs of conductive lines of the plurality of devices.

19. The apparatus of claim 17 wherein the computer system is semiconductor component circuitry.

20. The apparatus of claim 17 wherein the computer system is off-chip circuitry.

* * * * *